(12) United States Patent
Nomura et al.

(10) Patent No.: US 6,565,812 B1
(45) Date of Patent: May 20, 2003

(54) GAS SENSOR AND METHOD FOR PRODUCING IT

(75) Inventors: Tohru Nomura, Osaka (JP); Hideki Okoshi, Osaka (JP); Tomoko Yoshimura, Osaka (JP); Yutaka Kishimoto, Hyogo (JP); Yuichiro Tajiri, Osaka (JP)

(73) Assignee: Figaro Engineering Inc., Osaka (JP)

( * ) Notice: Subject to any disclaimer, the term of this patent is extended or adjusted under 35 U.S.C. 154(b) by 338 days.

(21) Appl. No.: 09/702,698

(22) Filed: Nov. 1, 2000

(30) Foreign Application Priority Data

Nov. 2, 1999 (JP) ............................. 11-312042

(51) Int. Cl.⁷ .................... G01N 27/00; G01N 21/00
(52) U.S. Cl. ...................... 422/98; 422/83; 422/94; 422/95; 422/96; 422/97; 338/34; 29/592; 29/592.1
(58) Field of Search ................. 422/98, 83, 94, 422/95, 96, 97; 324/468; 338/34; 29/592, 592.1, 700

(56) References Cited

U.S. PATENT DOCUMENTS 4,013,943 A * 3/1977 Chou et al. ................ 324/468
4,260,978 A * 4/1981 Yasuda et al. ............... 338/34
4,294,801 A * 10/1981 Segawa et al. ............. 422/98
4,849,180 A * 7/1989 Fukui ......................... 422/98

FOREIGN PATENT DOCUMENTS

JP 61-264246 11/1986

OTHER PUBLICATIONS

"FIS Gas Sensor SB–95 for carbon monoxide and methane detection", FIS Inc. (A printout from the Home Pages of FIS Inc.).

* cited by examiner

Primary Examiner—Jill Warden
Assistant Examiner—Brian Sines
(74) Attorney, Agent, or Firm—Rothwell, Figg, Ernst & Manbeck

(57) ABSTRACT

A base is provided with a concave and three leads, and the central lead is bent to the side opposite to the concave, and the other leads are bent to the side of the concave. A central electrode of a sensor element is attached to the central lead and the bottom of the concave and a coil serving as both a heater and an electrode is attached to the other leads to support the sensor element on a small base at four points.

9 Claims, 9 Drawing Sheets

GAS SENSOR AND METHOD FOR PRODUCING IT

DETAILED DESCRIPTION OF THE INVENTION

1. Field of the Invention

The present invention relates to a gas sensor herein a central electrode is passed through a coil serving as both a heater and an electrode and the coil is buried in a metal oxide semiconductor bead, and to a method of production thereof

2. Prior Art

The present applicant proposed a gas sensor wherein a central electrode is passed through a coil serving as both a heater and an electrode and they are buried in a bead of a metal oxide semiconductor and one end of the central electrode and both ends of the coil are attached to pins to provide three-point support to the bead (Japanese Patent Opening Sho 61-264246). Such a sensor, however, has an insufficient mechanical strength because of its three-point support, and it is difficult to position accurately the central electrode in relation to the coil.

3. Summary of the Invention

The object of the present invention is to provide a gas sensor of which mechanical strength is high and of which dispersions of characteristics such as sensor resistance are small, and a method of production thereof.

According to the present invention, a metal oxide semiconductor bead in which a coil and a central electrode are buried is supported above a concave provided in a base, and both ends of the coil are attached to two of three leads of the base. Now, if the central electrode can be positioned in the center of the coil, dispersions of resistance, etc. of the gas sensor will be reduced. The central electrode can be positioned by, for example, guiding both ends thereof out of the base and using chucks, etc. Alternatively, one end of the central electrode can be positioned by the remaining central lead of the three leads, and the other end thereof can be positioned by holding it above the concave or outside the base. Thus dispersions of the gas sensor characteristics can be reduced.

One end of the central electrode is fixed on the lead, and the other end thereof is fixed on the surface of the base or in the concave or on another lead. Accordingly, the sensor element is provided with four-point support, and this support significantly increases the mechanical strength in comparison with the three-point support.

In molding the base, the three leads are provided in plate forms, they are made to penetrate, in parallel with each other, the base within the same plane, the central lead is bent towards the side opposite to the concave, and the other two leads are bent towards the side of the concave. In this way the base having a concave can be molded easily together with the leads. A smaller base can be used by efficiently allotting the principal face of the base to an area for locating the three bent leads and an area for the concave.

If the concave is extended to one side face of the base and the other end of the central electrode is attached to the bottom of the base, handling of the central electrode can be facilitated and a larger concave can be provided. Moreover, as the central electrode bends between the bottom of the concave and the coil, some slack will be generated in its length, and this in turn will increase the resistance of the gas sensor to impacts of fall, etc.

Means for giving some slack to the central electrode are not limited to attachment of one end of the central electrode to the bottom of the concave. Provision of a bend between the attachment and the inside of the coil will do.

According to the production method of the gas sensor of the present invention, both ends of the coil are attached to the leads on both sides of the concave of the base, the central electrode is passed through the coil and positioned in relation to the coil, then a bead is formed. With this arrangement, dispersion of the clearance between the central electrode and the coil can be reduced, and the sensor characteristics can be made more even. Moreover, as both ends of the central electrode are fixed, the sensor element is supported by four points, and its mechanical strength is increased.

As for positioning of the central electrode, for example, both ends of the central electrode are chucked and positioned, or one end thereof is positioned on a lead and the other end is chucked and positioned.

If a thin wire is used for the central electrode to reduce the power consumption, it will be difficult to cut off the central electrode without generating any distortion and to pass the central electrode straight through the coil. Hence the wire of the central electrode is let out of a capillary, and the capillary is made to move forward to pass the wire through the coil. Next, the top end of the wire is held and the capillary is made to retreat so as to let out the wire from the capillary. After that, when the wire is locally melted for cutting the wire off, balls will be generated in the melted portions. Thus the wire can be cut off without generating any distortion in the wire. The wire having a ball at the top end thereof and being free of any distortion can be easily passed straight through the coil. In this way, the wire of the central electrode is passed through the coil, let out of the capillary and provided with a ball at the top end thereof

EMBODIMENT

Figure 1:
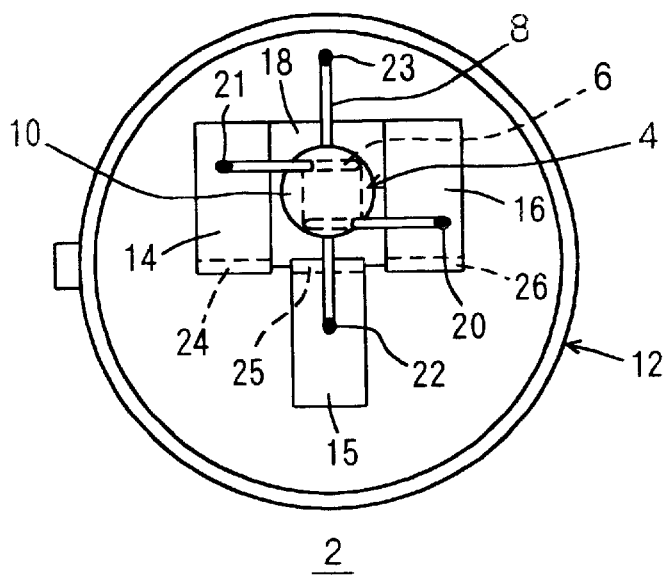
FIG. 1 is a plan view of the essential part of an embodiment of the gas sensor.
Figure 2:
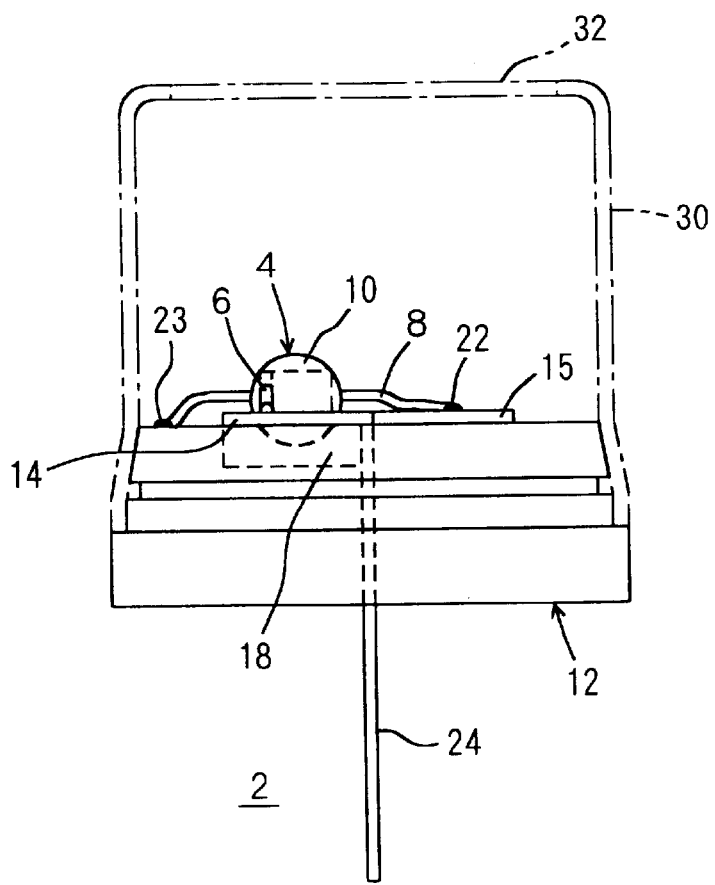
FIG. 2 is a side view of the essential part of the embodiment of the gas sensor.

FIG. 1 through FIG. 5 show an embodiment. FIG. 1 is a plan view of the essential part of the gas sensor and FIG. 2 is a side view thereof. 2 denotes a gas sensor, 4 denotes its sensor element wherein a central electrode 8 is passed through the center of a coil 6 serving as both a heater and an electrode and the coil 6 and the central electrode 8 are buried in a bead 10 of a metal oxide semiconductor, such as SnO2, of which resistance changes according to the level of a gas. The metal oxide semiconductor is not limited to SnO2. It may be ZnO, In2O3, WO3, etc. As for the materials for the coil 6 and the central electrode 8, wires of Pt, which can be easily welded although as its thermal conductivity is high its use results in a higher power consumption, and of noble metal alloys of which thermal conductivities are lower and their power consumptions are smaller, such as Pt-W, Pt-Cr, Pt-Au, Au-Pd-Mo and Pt-ZGS (an alloy in which the grain boundary of Pt is stabilized by zirconia), are preferable.

12 denotes a base, and a synthetic resin base is used here, but it may be a glass base. 14, 15, 16 denote at least three metal leads, which are preferably plates in shape, and these leads are in the base 12 arranged in parallel with each other and substantially in the same plane. The leads are integrally provided at the time of molding the base 12 in such a way that their legs 24, 25, 26 penetrate through the base 12. As shown in FIG. 2, the three legs are arranged in parallel with each other in the same plane, and at the time of molding these legs are set in parallel with the molds and the base 12 is molded. 18 denotes a concave, which is provided at the time of molding the base. The size of the concave is, for example, 1 mm wide×2 mm long×1 mm deep.

Of the three leads 14 through 16, the central lead 15 is bent towards the side opposite to the concave 18 and the leads 14, 16 on both sides are bent towards the direction opposite to that of the central lead 15 so that the bottoms of these leads will come into contact with the surface of the base. The edges of these leads are made in parallel with the concave 18. With this arrangement, the length in the direction of the diameter of the base 12 can be used effectively, and, in turn, a smaller base can be used.

20 through 23 are connections of the coil 6 and the central electrode 8. Of these connections, 20 through 22 are made by attaching portions near the both ends of the coil 6 and a portion near the one end of the central electrode on the leads 14 through 16 by conventional parallel gap welding. The connection 23 is made by applying the heat generated by the parallel gap welding current to a portion near the other end of the central electrode 8 to fuse the nearby base and attach the portion near the other end of the central electrode 8 to the base. These connections support the bead 10 above the concave 18. The portion near the other end of the central electrode 8 may be attached to another lead that is provided in addition to the above-mentioned three leads. Attachment is not necessarily limited to welding. It may be achieved by, for example, thermosonic bonding. The connection 23 may be made by an adhesive. In FIG. 1, a cap is omitted, but when the gas sensor is to be used actually, a cap 30 that is illustrated by chain line in FIG. 2 is used. 32 denotes an opening, and a metal net for explosion protection is provided over this part.

Figure 3:
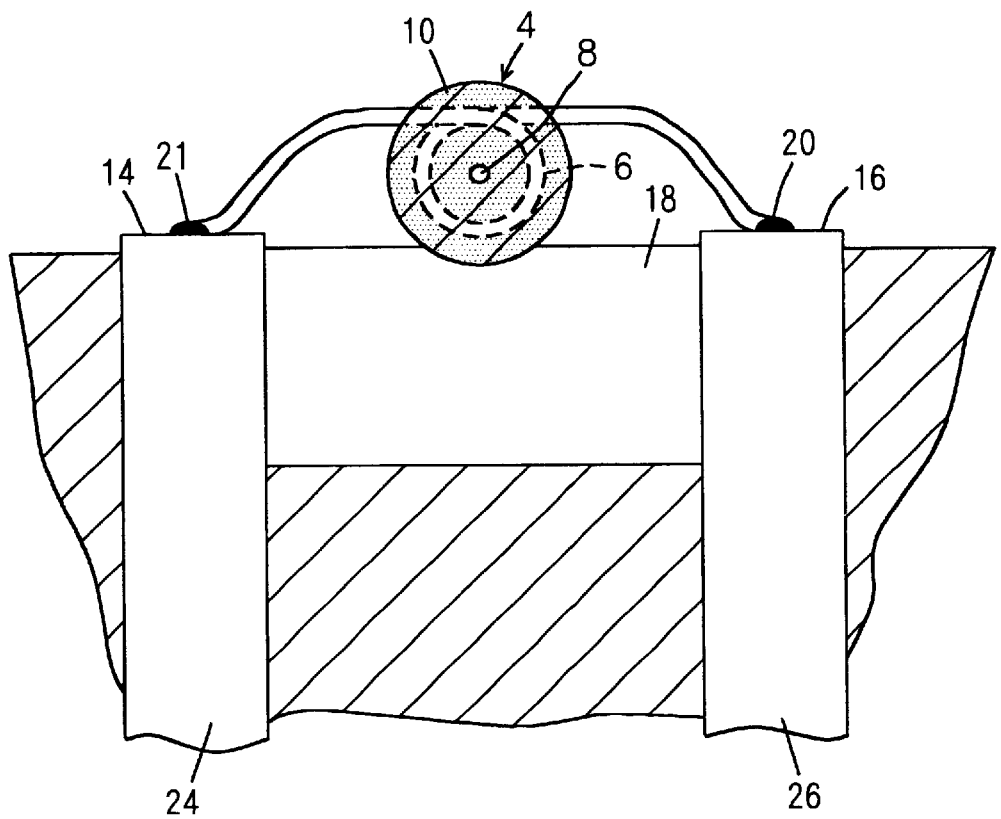
FIG. 3 is a sectional view showing the sensor element above the concave.
Figure 4:
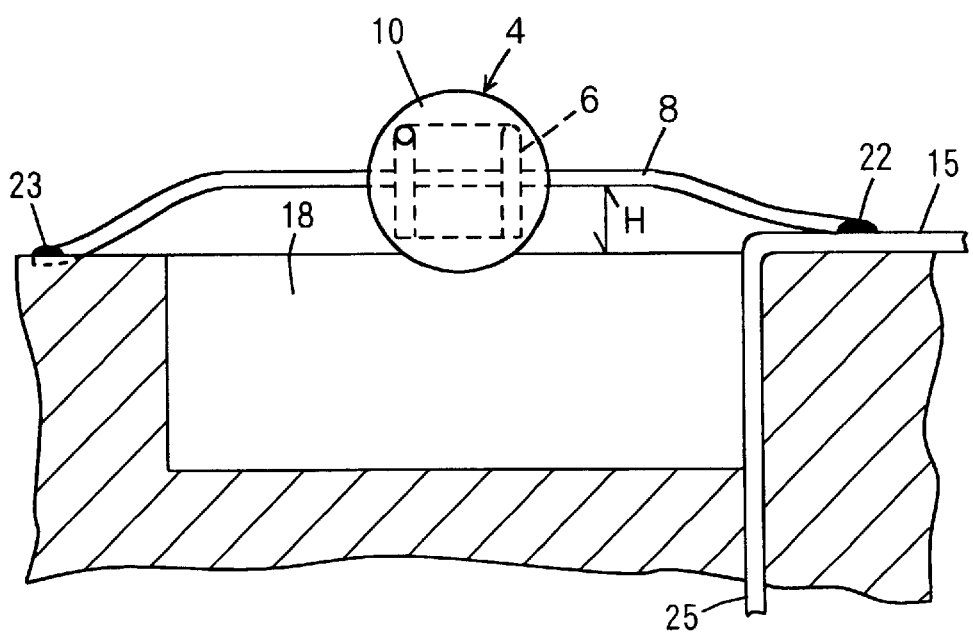
FIG. 4 is a side view showing the sensor element above the concave.

As shown in FIG. 3, portions near both ends of the coil 6 are attached to the leads 14, 16 by means of connections 20, 21 so as to hold the bead 10 above the concave 18. As the concave 18 is provided in the base, the coil 6 can be held with a smaller margin above the surface of the base than that without the concave 18. When the central electrode 8 is passed through the coil, the central electrode can be arranged at a height close to the surface of the base and this enables the central electrode to be attached to the base. As shown in FIG. 4, within the bead 10 or the coil 6, the central electrode 8 is lifted above the surface of the base 12 by about a height H. This will give some slack to the central electrode 8 and the central electrode 8 will be held in the coil 6 at a higher position, in comparison with the portions near both ends thereof, by H from the base surface.

Figure 5:
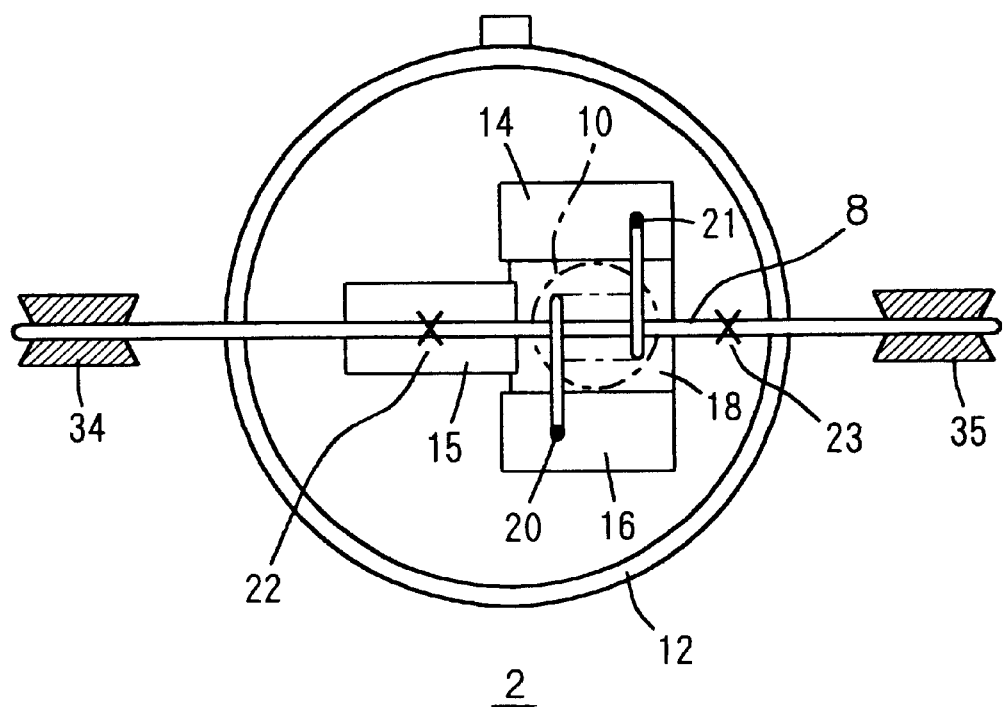
FIG. 5 is a plan view showing chucks for the central electrode.

With reference to FIG. 5, the method of production of the sensor 2 will be described. First, three legs 24 through 26 of three leads 14 through 16 are arranged in parallel with each other in the same plane and are connected to a tiebar not illustrated. A total of three molds comprising two molds from the left and the right of FIG. 5 and a mold for providing the concave 18 are used to integrally mold the base 12 with leads 14 through 16 with a resin, etc. Then the central lead 15 is bent towards the side opposite to the concave 18, and leads on both sides 14, 16 are bent in the direction opposite to that of the central lead 15 so that the bottoms of the respective leads will substantially come into contact the surface of the base 12. Bending of the leads 14 through 16 may be done before molding or after molding; either will do.

Next, the coil 6 is attached to the leads 14, 16 by the connections 20, 21 by parallel gap welding. Then the central electrode 8 is passed through the center of the coil 6, the central electrode 8 is positioned by chucks 34, 35 located on both outer sides of the base 12, and the central electrode 8 is attached by the connections 22, 23 by parallel gap welding. After that, the bead 10 is molded and sintered. Or reversely, the bead 10 may be formed while the central electrode 8 is being held by the chucks 34, 35, and after that the central electrode 8 may be attached by the connections 22, 23.

According to the method of production of the sensor of the present invention, as the leads and the base can be integrally molded, the cost of producing the base can be reduced. As the surface of the base can be utilized effectively, a smaller base can be used. Moreover, as the central electrode 8 can be chucked from both sides and its position can be adjusted finely, positioning the central electrode 8 is facilitated, and the central electrode 8 can be located at the center of the coil 6.

Figure 6:
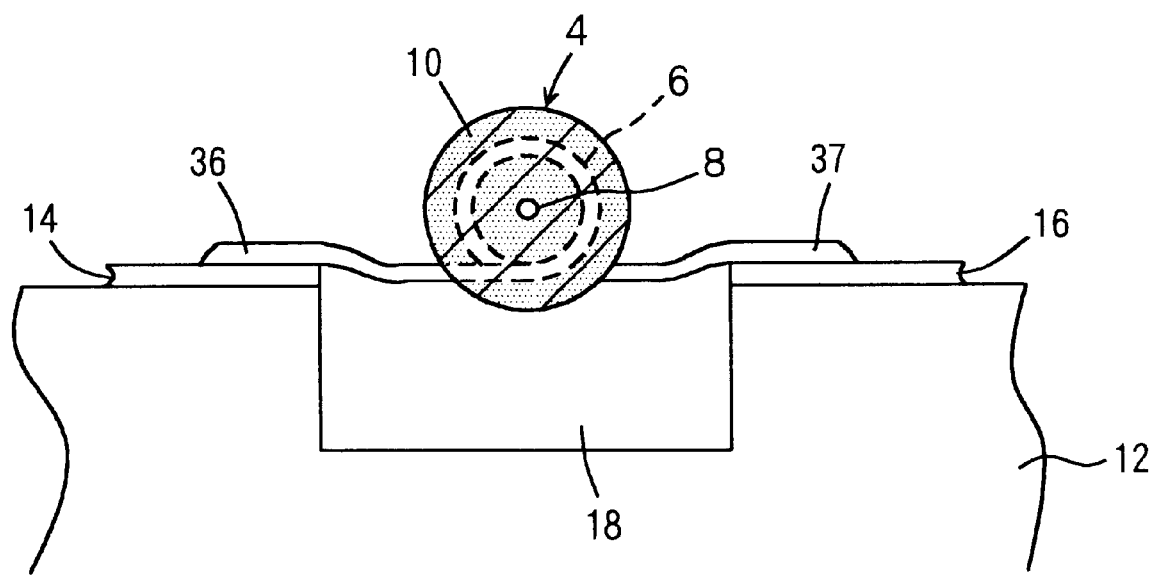
FIG. 6 is a sectional view showing a modification concerning the sensor element.

FIG. 6 shows a modification concerning the sensor element. As bent portions are naturally generated between the coil 6 and the connections 20, 21, vibrations and impacts were absorbed by these bent portions, and breakage of the coil 6 was almost nil. In contrast to this, breakage concentrated in the central electrode 8. Hence, as shown in FIG. 6, prolongations 36, 37 from the coil 6 to the connections 20, 21 that are almost straight may be used.

Figure 7:
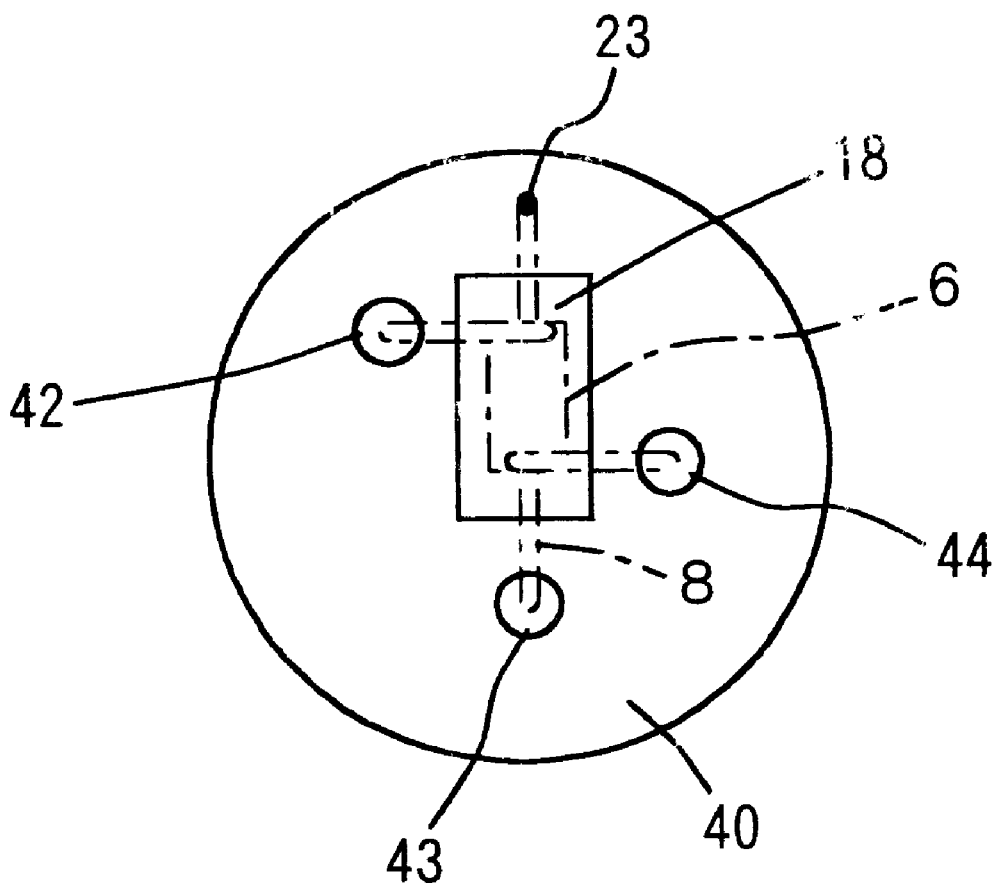
FIG. 7 is a plan view showing a modification concerning the base.

FIG. 7 shows a modification concerning the base. In this modification, three metal pins 42 through 44 are driven into a resin base 40, and a concave 18 is provided similarly. Other arrangements are similar to those of the embodiment. When compared with the base 12 of FIG. 1 through FIG. 5, this base has an increased cost by that required for driving the pins 42 through 44.

Test

A drop test was made to examine the strength of the gas sensor 2. The sensors that were used in the test were produced as follows: The inner diameter of the coil 6 is 150 $\mu$m, the length of the coil 6 is also 150 $\mu$m, and the bead 10 is almost spherical and about 250 $\mu$m in diameter. As shown in FIG. 5, the central electrode 8 was passed through the center of the coil 6 and chucked, and after that, the central electrode 8 was attached by the connections 22, 23. The central electrode 8 was lifted, as described above, by a height H from the base so as to give some slack to it. After attaching the central electrode 8, a paste of powder of SnO2 was made, and the paste was applied, dried and sintered at temperatures ranging from 600 to 750° C. to produce the bead 10. Both the central electrode 8 and the coil 6 were Pt-W wire of 15 μm in diameter.

The power consumption to heat the gas sensor 2 that was produced as described above at a constant temperature of 500° C. was 60 mW approx. When the connection 23 was made on a metal rather than on the base, the power consumption increased by 3 mW. In this case, however, Pt-W wire, of which thermal conductivity is low, was used for the central electrode 8. When Pt wire of the same diameter was used for the central electrode 8 and the connection 23 was made on a metal, the power consumption increased by 10 mW approx. Thus the power consumption of the sensor was reduced successfully by making the connection 23 on a resin base to reduce the loss of heat of the heater.

In the drop test, metal caps were put on twelve samples of the sensor 2 of each of the respective types, and the samples were made to fall on a concrete floor from a height of 1 m for 30 times. After the falls, the samples of the sensors were examined to count the numbers of samples that had breakage of the central electrode 8, deformation of the coil 6, and breakage of the bead 10, respectively.

The results of the drop test are shown in Table 1. Here the control 1 is a gas sensor in which the connection 23 is not attached so as to provide three-point support. The control 2 is a gas sensor in which the connection 23 is not attached and the position of the central electrode in the coil 6 and the elevation of the central electrode on the lead 15 are aligned.

TABLE 1

| Sample | Drop Test | | |
|---|---|---|---|
| | Coil deformation | Bead breakage | Central electrode breakage |
| Embodiment (4-point support) | 1 | 1 | 0 |
| Control 1 (3-point support) | 8 | 4 | 0 |
| Control 2 (3-point support and no lift of the central electrode) | 7 | 3 | 2 |

* The number of samples of each was 12. Both the central electrode and the coil were Pt-W wire of 15 μm in diameter. The capped gas sensors were dropped from a height of 1 m down to a concrete floor for 30 times.

As shown in Table 1, the controls 1, 2 exhibited many instances of coil deformation and bead breakage, and the control 2 also exhibited breakage of the central electrode. In contrast to them, the embodiment of the present invention exhibited few instances of both coil deformation and bead breakage, and breakage of the central electrode was nil.

The Best Embodiment

Figure 8:
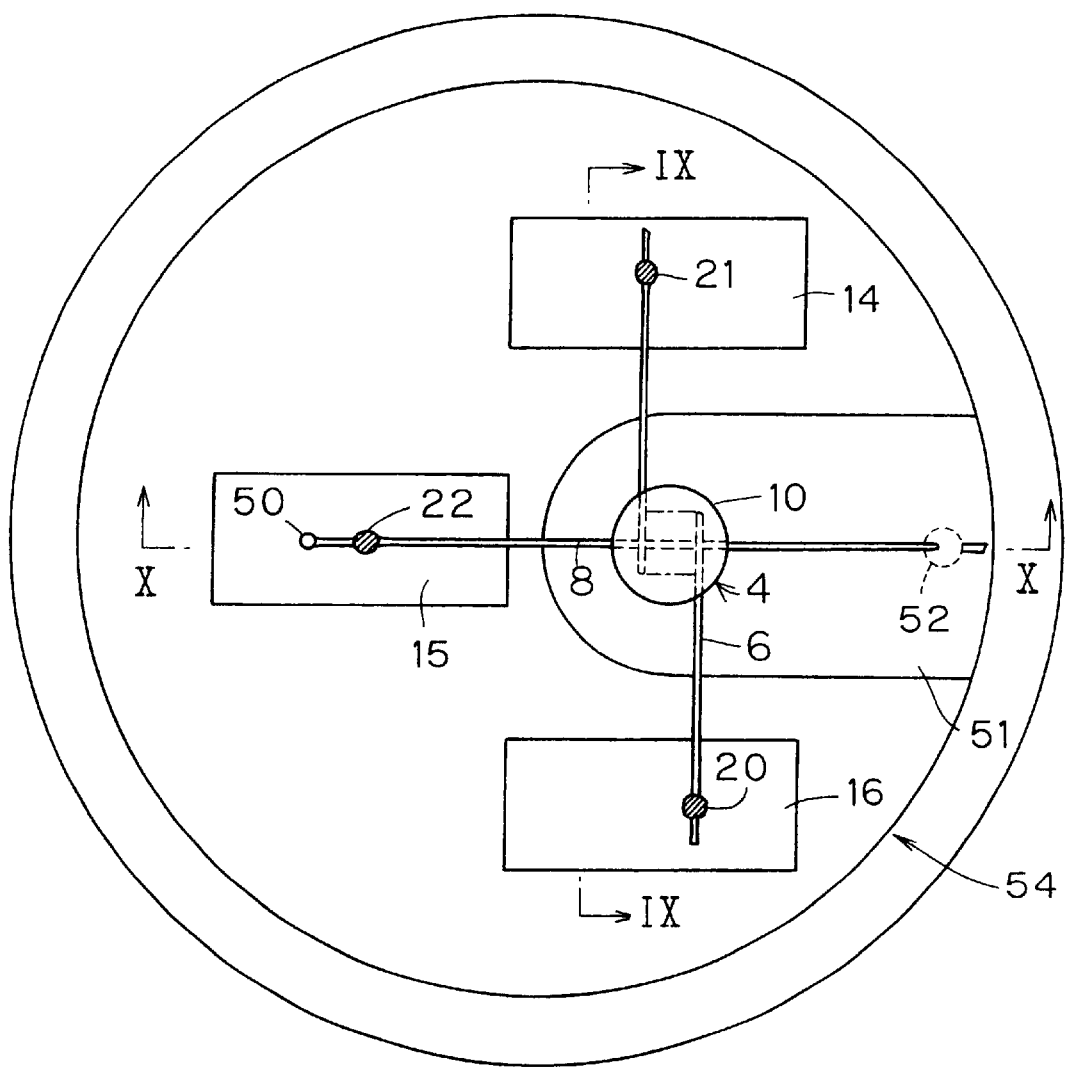
FIG. 8 is a plan view of the best embodiment of the gas sensor.
Figure 9:
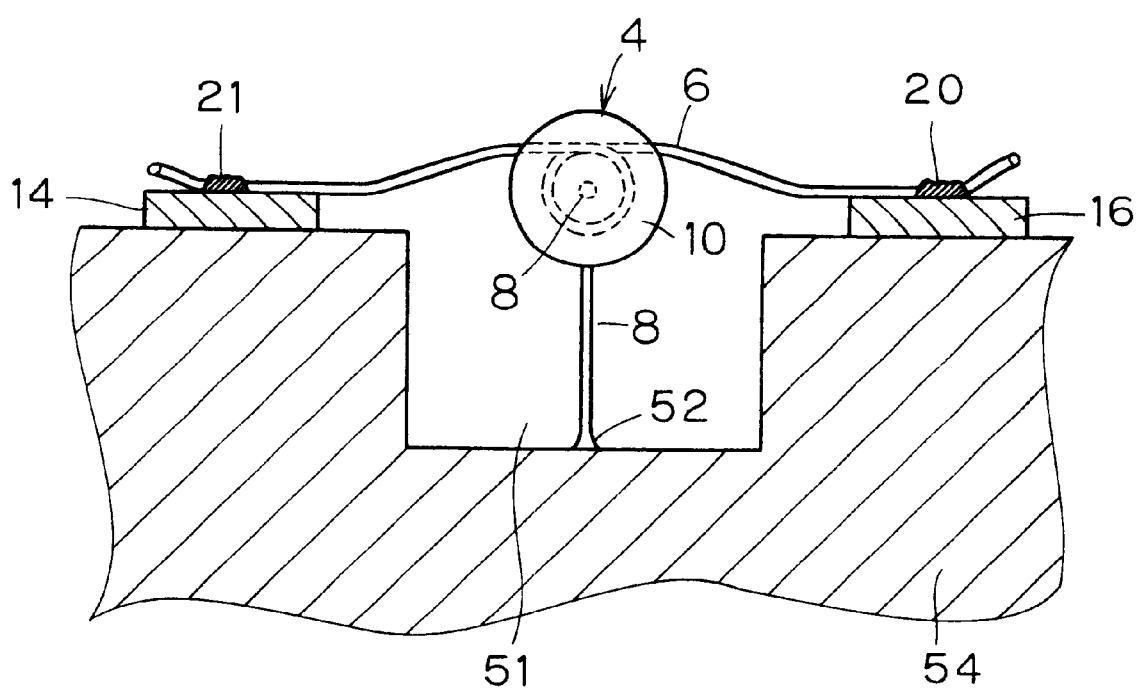
FIG. 9 is a sectional view of the essential part of the gas sensor of FIG. 8 along the line IX—IX.
Figure 10:
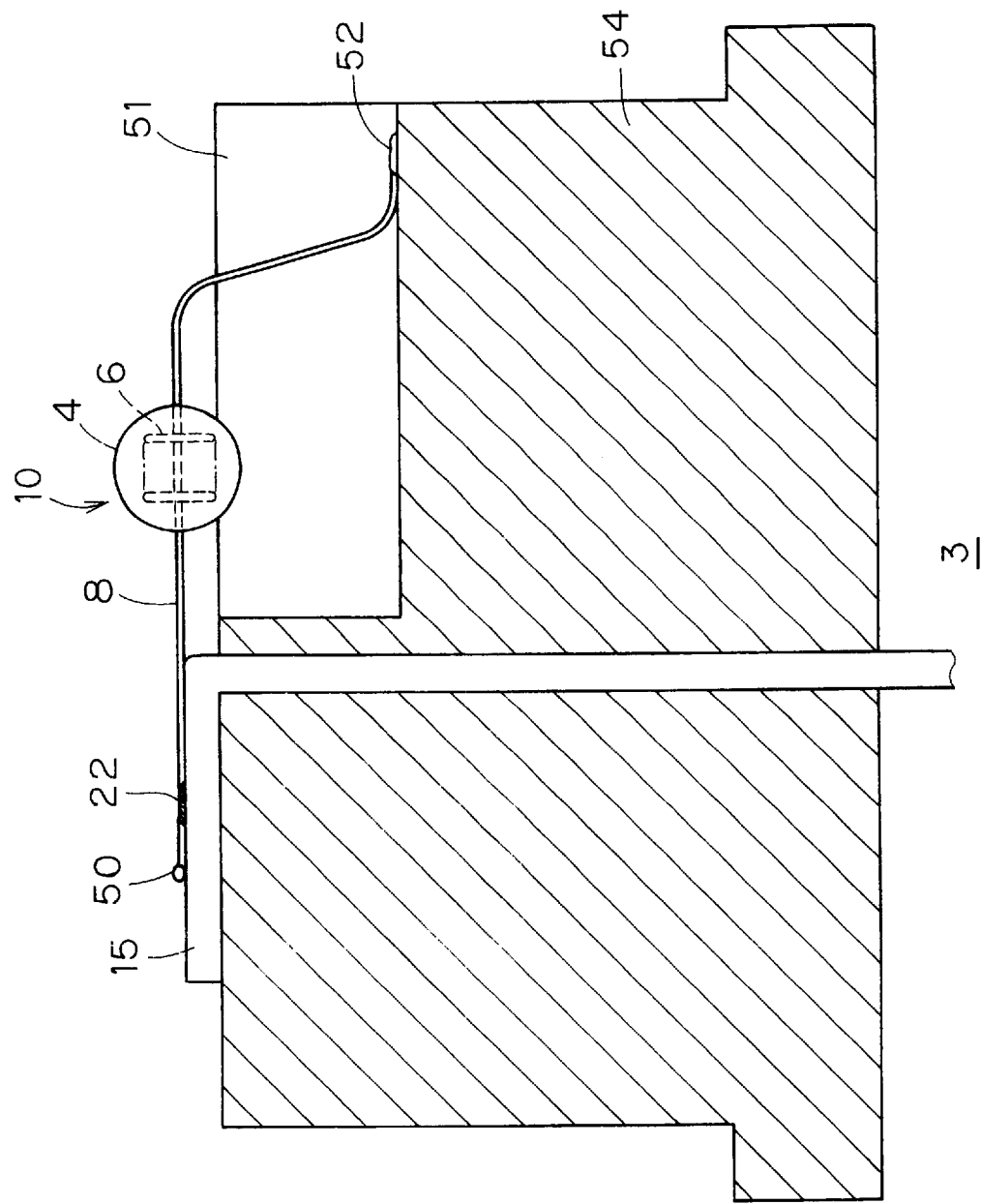
FIG. 10 is a sectional view of the essential part of the gas sensor of FIG. 8 along the line X—X.

FIG. 8 through FIG. 12 show the best embodiment. FIG. 8 through FIG. 10 show the construction of a completed gas sensor 3 that is similar to the embodiment of FIG. 1 through FIG. 5 except some specific points. The same marks with the embodiment of FIG. 1 through FIG. 5 denote the same objects. 4 denotes a sensor element and 10 denotes a bead. 6 denotes a coil and 8 denotes a central electrode. The bead 10 may have, for example, a spherical shape of which diameter is about 300 μm, or an eggshell shape of which minor axis is about 300 μm and major axis is about 400 μm. As for the materials of the coil 6 and the central electrode 8, wires of Pt, Pt-W, Pt-Cr, etc. of from 15 to 20 μm in diameter are used. 54 is a base of a resin. 14 through 16 are metal leads.

Both ends of the coil 6 are attached to the leads 14, 16 by the connections 20, 21 by, for example, parallel gap welding. There is a ball 50 at the top end of the central electrode 8, and the ball 50 was produced by fusion. The central electrode 8 is attached on the lead 15 at a connection 22 that is away from the ball 50 towards the bead 10. In connecting the central electrode 8 to the lead 15, for example, parallel gap welding may be used. The central electrode 8 may be cut off between the ball 50 and the connection 22. 51 denotes a concave provided in the base 54, and the bead 10 is above the concave 51. The other end of the central electrode 8 is bent towards the bottom of the concave 51 and fixed to the bottom of the concave 51 by a connection 52.

FIG. 9 shows in section the bead 10 along the line IX—IX of FIG. 8. The elevations of both ends of the coil 6 are substantially identical, and due to the elasticities in the coiling-starting portion and the coiling-ending portion of the coil 6, the coil 6 is fixed in such a way that the top of the coil 6 is lifted a little from the level of the surfaces of the leads 14, 16. As a result, when the central electrode 8 is passed through the center of the coil 6, the central electrode 8 will come just on the surface of the lead 15. As shown in FIG. 9, the other end of the central electrode 8 is bent on the side of the connection 52.

FIG. 10 shows the section along the line X—X of FIG. 8. The central electrode 8 is passed through the center of the coil 6, bent on the side of the connection 52 and fixed.

Figure 11:
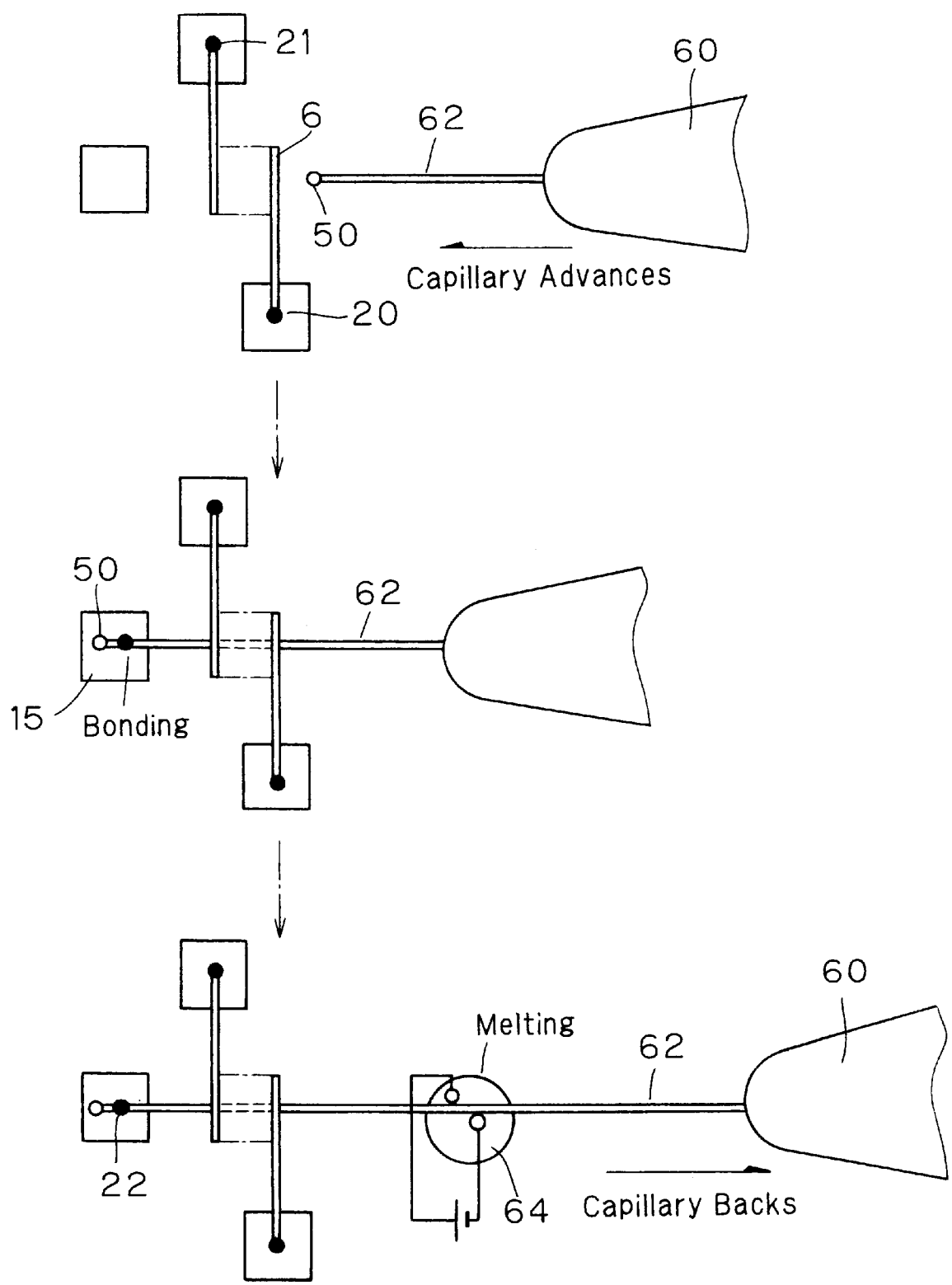
FIG. 11 is a production process diagram of the best embodiment of the gas sensor.
Figure 12:
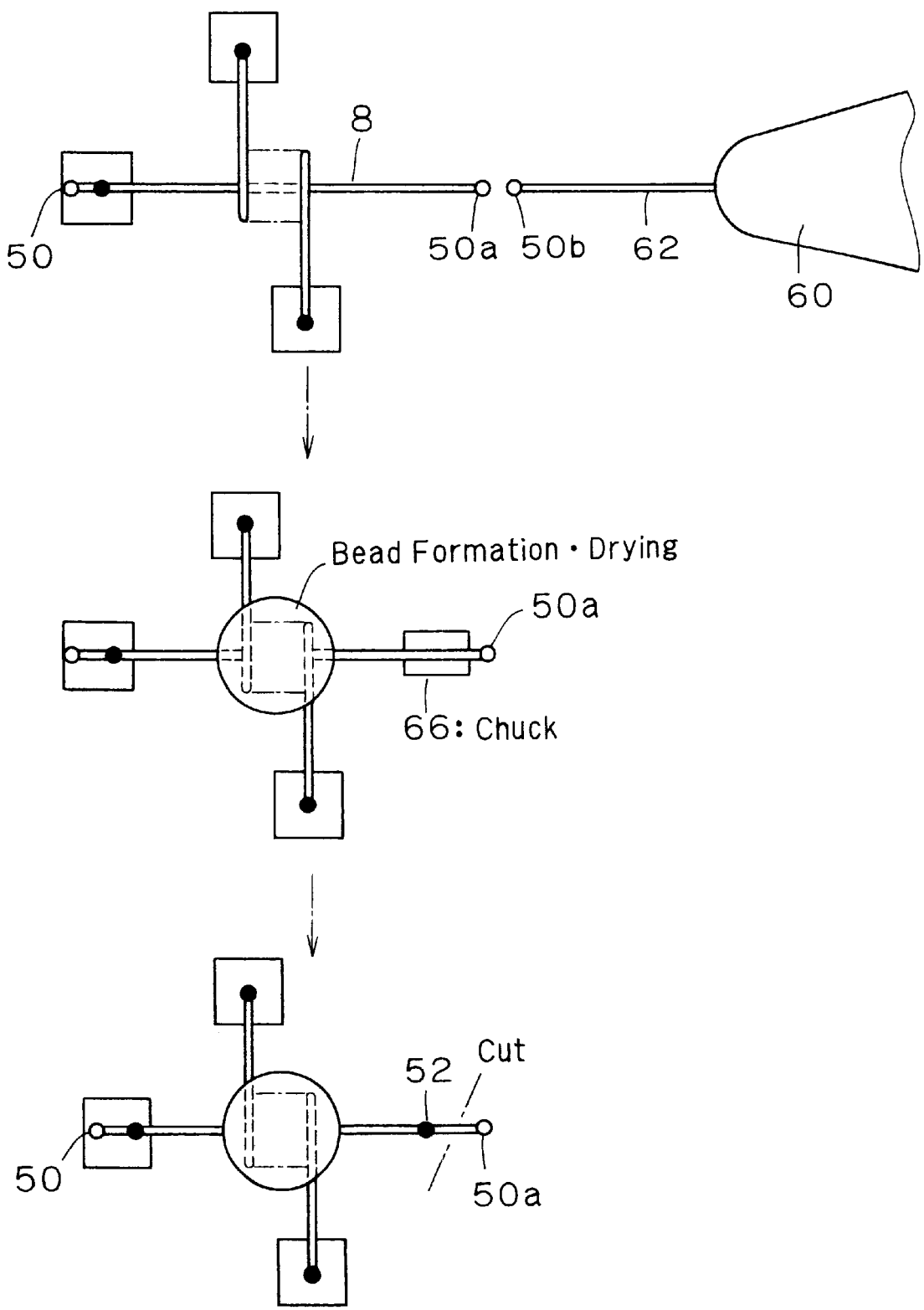
FIG. 12 is a production process diagram showing steps beyond those shown in FIG. 11.

FIG. 11 and FIG. 12 show the production process of the gas sensor 3 of the best embodiment. Presentation of FIG. 11 and FIG. 12 is schematic and the sizes are not proportional to the actual sizes. Both ends of the coil 6 are welded to the leads 16, 14 by the connections 20, 21. Next, a wire 62 having a ball 50 that is formed at the top end thereof is let out of a capillary 60, and the capillary 60 is made to advance towards the coil 6. In this way, the ball 50 is made to pass through the coil 6, and the wire 62 is attached by, for example, parallel gap welding, on the lead 15 at a point a little short of the ball 50. Next, when the capillary 60 is made to move backwards, as the wire 62 is connected by the connection 22, the wire 62 will be let out.

Next, a melting device 64 is used to melt and break the wire 62. This generates a pair of balls 50a, 50b, and the ball 50b will serve as the ball at the top end of the next wire. The point of melting is determined by the required length of the wire that has been let out of the nozzle of the capillary 60 to fully pass through the coil 6. After that, the ball 50a side of the wire is held by, for example, a chuck 66, and a bead 10 is formed and dried. This will fix the position of the central electrode 8 in the bead 10. Then the ball 50a side of the wire is lowered to the bottom of the concave by the chuck 66. Then the wire is fixed at the connection 52 by applying electric current to the wire to generate heat and fuse the resin of the base or using an adhesive. If necessary, the central electrode is cut off between the ball 50a and the connection 52. After that, when the bead 10 is sintered, the gas sensor 3 will be obtained.

Here after the central electrode 8 is fixed on the lead 15 by the connection 22 the other end of the wire is chucked. However, both ends of the wire may be chucked to form balls 50a, 50b and make and dry the bead. Sintering of the bead 10 may be done at any time provided that it is done after drying the bead 10. The coil 6 and the central electrode 8 may be connected to the leads by not only parallel gap welding but also any bonding method.

What is claimed is:

1. A gas sensor having a sensor element wherein a central electrode is passed through a coil serving as both a heater and an electrode and the coil and the central electrode are buried in a bead of a metal oxide semiconductor characterized in that the gas sensor has a base having at lest three leads and a concave, both end portions of said coil and one end portion of said central electrode are attached on said leads, said bead is held above said concave, said at least three leads are in plate form, said leads are made to penetrate, in parallel with each other, the base in essentially the same plane, and on the base a central lead of the three leads is bent towards the side opposite to the said concave and the leads on both sides of the central lead are bent in a direction opposite to the central lead.

2. A gas sensor of claim 1 characterized in that said three leads and said concave are exposed on one principals face of said base, said base has at least a side face around said principal face, and said concave extends to said side face on the opposite side of said central lead to form an opening in said side face.

3. A gas sensor of claim 2 characterized in that the other end of said central electrode is attached on the bottom of said concave.

4. A gas sensor of claim 1 characterized in that said central electrode is bent between an end portion thereof and the inside of said coil.

5. A method for producing a gas sensor having a sensor element wherein a central electrode is passed through a coil serving as both a heater and an electrode and the coil and the central electrode are buried in a bead of a metal oxide semiconductor characterized by a step of providing a base that has a concave and at least three leads on one principal face, arranging two of said three leads on both sides of the concave, and arranging one lead between said two leads and outside the concave;

a step of attaching both ends of said coil on said two leads;

a step of passing said central electrode through said coil, and a step of forming a bead of a metal oxide semiconductor to bury said coil and said central electrode therein, wherein the above steps are executed in the above order, and one end of said central electrode is connected on said one lead.

6. A method for producing a gas sensor of claim 5 characterized in that, in said step of positioning said central electrode, positioning is made by chucking at least one end of the central electrode.

7. A method for producing a gas sensor of claim 5 characterized in that said step of passing said central electrode through said coil comprises:

a step of providing the top end of a wire being let out of a capillary with a ball and advancing said capillary towards said coil to pass said wire through the coil;

a step of holding the central electrode having been passed through the coil and moving the capillary backwards to let the wire out .of the capillary; and a step of melting the wire on the side opposite to said ball in relation to the coil to form new balls.

8. The gas sensor of claim 1, wherein the other end portion of said central electrode is attached on the base or to a lead.

9. The method of claim 5, wherein the other end of said central electrode is connected on said base or to a lead.

* * * * *